(12) United States Patent
Hentschel-Bukman et al.

(10) Patent No.: US 8,035,496 B2
(45) Date of Patent: Oct. 11, 2011

(54) METHOD AND COMPUTER PROGRAM FOR IDENTIFICATION OF INATTENTIVENESS BY THE DRIVER OF A VEHICLE

(75) Inventors: Elisabeth Hentschel-Bukman, Magstadt (DE); Arnim Lars Galley, Berlin (DE); Klaus-Peter Kuhn, Pluederhausen (DE); Dietmar Neumerkel, Berlin (DE)

(73) Assignee: Daimler AG, Stuttgart (DE)

( * ) Notice: Subject to any disclaimer, the term of this patent is extended or adjusted under 35 U.S.C. 154(b) by 706 days.

(21) Appl. No.: 10/580,858

(22) PCT Filed: Nov. 13, 2004

(86) PCT No.: PCT/EP2004/012888
§ 371 (c)(1), (2), (4) Date: Dec. 19, 2008

(87) PCT Pub. No.: WO2005/059857
PCT Pub. Date: Jun. 30, 2005

(65) Prior Publication Data
US 2009/0115589 A1 May 7, 2009

(51) Int. Cl.
*B60Q 1/00* (2006.01)
(52) U.S. Cl. ............ 340/439; 340/575; 340/576; 701/1; 701/301; 180/272
(58) Field of Classification Search .................. 340/439, 340/575, 576; 701/1, 301; 180/272
See application file for complete search history.

(56) References Cited

U.S. PATENT DOCUMENTS

| | | | | |
|---|---|---|---|---|
| 4,594,583 A | * | 6/1986 | Seko et al. | 340/576 |
| 5,745,031 A | | 4/1998 | Yamamoto | |
| 5,754,031 A | * | 5/1998 | Kanazawa et al. | 322/28 |
| 6,061,610 A | * | 5/2000 | Boer | 701/1 |

FOREIGN PATENT DOCUMENTS

| | | |
|---|---|---|
| DE | 25 46 345 | 4/1977 |
| DE | 198 18 239 A1 | 10/1999 |
| EP | 0 147 539 A2 | 9/1983 |
| EP | 0 952 039 A2 | 10/1999 |
| JP | 58-23713 Y2 | 5/1983 |
| JP | 62-34212 B2 | 7/1987 |
| JP | 62-34215 B2 | 7/1987 |
| JP | 4-274935 A | 9/1992 |
| JP | 7-93678 A | 4/1995 |
| JP | 2001-273594 A | 10/2001 |
| JP | 2002-225586 | 8/2002 |

OTHER PUBLICATIONS

International Search Report dated Feb. 15, 2005 including English Translation of Relevant Portion (Five (5) pages).
Notice of Reason for Refusal dated Apr. 16, 2007 (Three (3) pages).
Notice of Reason for Refusal dated Jul. 8, 2008 with an English translation (Four (4) pages).

* cited by examiner

*Primary Examiner* — Daryl Pope
(74) *Attorney, Agent, or Firm* — Crowell & Moring LLP (57) ABSTRACT

A method and a computer program for identifying when the driver of a vehicle, in particular a motor vehicle, is not paying attention. In order to make it possible to make a more reliable statement on the presence of any inattentiveness by the driver, the method observes a steering action following a steering quiescent phase, in addition to detecting the steering quiescent phase. The extent of the steering quiescent phase and of the steering action found are logically linked to one another, and the result of this logical operation is then used as a measure for the severity of the inattentiveness of the driver.

30 Claims, 6 Drawing Sheets

METHOD AND COMPUTER PROGRAM FOR IDENTIFICATION OF INATTENTIVENESS BY THE DRIVER OF A VEHICLE

BACKGROUND AND SUMMARY OF THE INVENTION

The invention relates to a method and a computer program for identifying when a driver of a vehicle, in particular a motor vehicle, is not paying attention during operation of the vehicle. The invention also relates to a data storage medium having stored thereon such a computer program.

Various proposals for detecting inattentiveness by a motor vehicle driver, in particular a tendency for the motor vehicle driver to go to sleep, are known from the prior art.

By way of example, one corresponding proposal is disclosed in German Laid-Open Application DE 198 18 239 A1. The apparatus disclosed there for warning that a motor vehicle driver is going to sleep comprises firstly a vehicle environment identification device for detection of the actual driving style of the motor vehicle driver. The apparatus described there also comprises a device for detection of a reference driving style, in particular detecting how many lateral self-movements there normally are by the motor vehicle driver in his driving style. Finally, the disclosed apparatus has comparison logic for comparison of the reference driving style with the current actual driving style in order to output a warning to the motor vehicle driver on the basis of the result of this comparison.

Furthermore, a method and an apparatus for determination of the stress of the driver of a motor vehicle are known from U.S. Pat. No. 6,061,610. This method provides for the steering wheel angle of the motor vehicle to be detected first of all in order from this to generate prediction errors for the steering wheel angle in the driver's control of the motor vehicle. A distribution of these prediction errors is then calculated in order to compare this distribution with another distribution of prediction errors of the steering wheel angle which does not represent the real steering behavior of the driver, but represents a predetermined steering behavior of a stress-free or unstressed driver. The result of this comparison then represents the current stress on the driver while driving the motor vehicle.

Finally, German Laid-Open Application Del. 25 46 345 discloses a driver warning device for warning motor vehicle drivers before they go to sleep. The device detects the steering movement of the driver of the motor vehicle, on the assumption that, when the driver is awake, the steering wheel is not held entirely at quiescent even when traveling in a straight line but that steering movements are also carried out continuously then, even if they are still very small. If the driver warning device detects absence of these steering movements over an adjustable time interval, as well, then the driver warning device deduces from this that the driver is going to sleep, or is at least at risk of going to sleep, and then warns the driver by outputting a signal.

The driver warning device disclosed in the last-mentioned Laid-Open Application DE 25 46 345 has a disadvantage in that the decision on when the driver of a vehicle is not paying attention is made solely on the basis of the detection of a steering quiescent phase, and that this decision can, therefore, be made only quite vaguely and unreliably.

Against the background of this prior art, the object of the invention is, therefore, to provide a method and a corresponding computer program in order to identify when the driver of a motor vehicle is not paying attention, as well as a controller for carrying out this method and a data storage medium storing such a computer program, which makes it possible to more reliably identify possible inattentiveness of the driver.

This object is achieved by a method for identifying when the driver of a vehicle, in particular of a motor vehicle, is not paying attention. The method includes detecting any movement of a steering wheel of the vehicle in the form of a steering wheel angle x; and identifying a steering quiescent phase and determining the magnitude of the extent of the steering quiescent phase by evaluating the detected steering wheel angle and/or its rate of change; wherein a steering action is identified following the steering quiescent phase and the magnitude of the extent of the steering action is determined by evaluating the rate of change of the steering wheel angle; and further wherein a measure of the severity of the inattentiveness by the driver is determined while steering the vehicle by assessing the result of a link between the extent of the steering quiescent phase and the extent of the steering action.

In the process of identification of inattentiveness of the driver, the invention—in contrast to the prior art—advantageously distinguishes between a steering quiescent phase and a more or less hectic steering action, which typically follows a state of inattentiveness. Thus, according to the invention, a state of inattentiveness is not assumed at all unless both the steering quiescent phase and the subsequent steering action are identified in conjunction with one another; conversely, this means that just identification of a steering quiescent phase or of a steering action is not sufficient to deduce inattentiveness of the driver. The detected extents of both the quiescent phase and of the steering action are logically linked to one another for determination of the extent of the severity of the inattentiveness, and the result is then assessed.

In modern vehicles, in particular motor vehicles, a sensor for detection of the steering wheel angle x is normally provided in any case. Thus, in principle, no additional sensors are advantageously required to implement the described method.

Two different exemplary embodiments for implementation of the invention will be explained in the description and claimed herein. In principle, a specific way to determine the extent of the steering quiescent phase is provided for a first of the exemplary embodiments; however, this determination process can also be carried out according to a second of the exemplary embodiments.

Further refinements of the method, as are described and claimed herein, apply equally both to the first exemplary embodiment and to the second exemplary embodiment.

Advantages of the First Exemplary Embodiment

Calculation of the extent of the steering action solely by formation of a steering wheel angle variance would merely represent the steering behavior of the driver at one time. However, in order to make a reliable statement on the existence of inattentiveness, it is in fact important to take account of changes in the steering behavior over time, as well. According to the invention, this aspect is taken into account by including two steering wheel angle variances in the formation of the variance ratio, which each represent the steering action of the driver at different times, with the two times being offset through a time interval $\Delta t$ with respect to one another.

The variance ratio calculated according to the invention can intrinsically advantageously be interpreted as a measure of the severity of the inattentiveness of the driver while steering the vehicle at the time $t_1$; inattentiveness of the driver exists in particular when this variance ratio has a value greater than 1.

Advantage of the Second Exemplary Embodiment

In contrast to the first exemplary embodiment, the second exemplary embodiment makes use of considerably fewer parameters for assessment of the inattentiveness of the driver. It is, therefore, less memory intensive. Furthermore, owing to the use of considerably simpler algorithms, it can be coped with more easily and can be implemented in real-time. Overall, it is therefore highly suitable for practical use in a vehicle.

It is thus advantageous that an assessment of the extent of the steering quiescent phase, that is to say its time duration, is preferably made only by evaluation of the steering wheel angle, and the extent of the steering action is preferably determined only by detection of the maximum steering angle wheel gradient that occurs. There is, therefore, no need for any calculation or evaluation based on the variance function.

Logically linking the extent of the steering quiescent phase to the extent of the steering action in order to determine a measure for the severity of the inattentiveness by the driver is carried out in the second exemplary embodiment by way of a multi-dimensional operator. In order to save unnecessary computation complexity, this logical operation is, however, preferably carried out only when both the steering quiescent phase and the expected subsequent steering action each take place with a predetermined minimum extent. If the steering quiescent phase or the steering action are not sufficiently sharply pronounced, then, according to the invention, it is assumed that the driver is not in a state of inattentiveness.

Advantageous Refinements of the Inventive Method which Both Exemplary Embodiments May Employ The result of the logical operation from the first or second exemplary embodiment, that is to say the variance ratio or the result of the operator logical operation, can advantageously be mapped onto a probability value with the aid of the sigmoid function. This means that it is possible to specify a probability of the driver having been inattentive in the steering of the vehicle at the time $t_1$ between 0 and 100%.

In a further advantageous refinement, the claimed method based on the previously determined probability value allows a statement to be made on the probability with which the behavior of the driver can be associated with one specific fatigue level, which is suitably selected and is predetermined from a large number of such levels. According to the invention, an association such as this is always made taking into account the currently detected steering wheel angle.

This association with the predetermined fatigue levels can advantageously be made more precise by taking into account not only the steering wheel angle as a first indicator, but also further observable indicators for the inattentiveness by the driver, such as his eyelid closure behavior or his reaction time.

It is also advantageous that the estimate of the fatigue of the driver can also be made more precise by taking account for this estimate not only the currently detected values of, in particular, the stated indicators, but also the fatigue classifications carried out in the recent past. In other words, this procedure allows a plausibility check of the new estimate taking into account the fact that the driver fatigue is not a phenomenon which occurs or disappears again suddenly, but which in fact changes only continuously over the course of time.

The inventive method advantageously allows not only, as described above, a conclusion to be drawn about driver fatigue as the cause of the detected inattentiveness. In fact, it also allows a conclusion to be drawn relating to other causes for the detected inattentiveness, which, for example, may lie in a conversation being held with a front seat passenger or the operation of an apparatus, such as the radio or the glove compartment in the vehicle.

In order to improve the reliability of a statement relating to the attention level or inattentiveness of the vehicle driver, it is worthwhile evaluating not only a result of the logical operation according to the first or second exemplary embodiment but, instead of this, for this statement to be based on a large number of such logical operation results. In this case, this plurality may include not only merely results from the first or from the second exemplary embodiment, but also a mixture of results from the first and from the second exemplary embodiment. Specifically, a statement can be made more reliably about the inattentiveness by the driver by weighting each result obtained from a logical operation with an associated weighting factor in order then to obtain an averaged logical operation result in the final analysis from the present plurality of weighted logical operation results, by mathematical averaging. This averaged logical operation result then represents a more reliable measure than a non-averaged logical operation result of the severity of the inattentiveness by the driver in the steering of the vehicle at a specific time.

Finally, it is advantageous, in particular, for the driver of the vehicle to be informed of the identified inattentiveness in the form of visual or audible warning information.

Further advantageous refinements of the method are described and claimed herein.

The object of the invention as mentioned above is also achieved by a computer program for carrying out the described method, by a data storage medium with the computer program, and by a controller for carrying out the described method. The advantages of these solutions correspond to the advantages mentioned above with respect to the described method.

This computer program advantageously need be programmed only once at least for individual vehicle types, and can then be implemented in all the vehicles of a corresponding model.

DETAILED DESCRIPTION OF THE DRAWINGS

Figure 1:
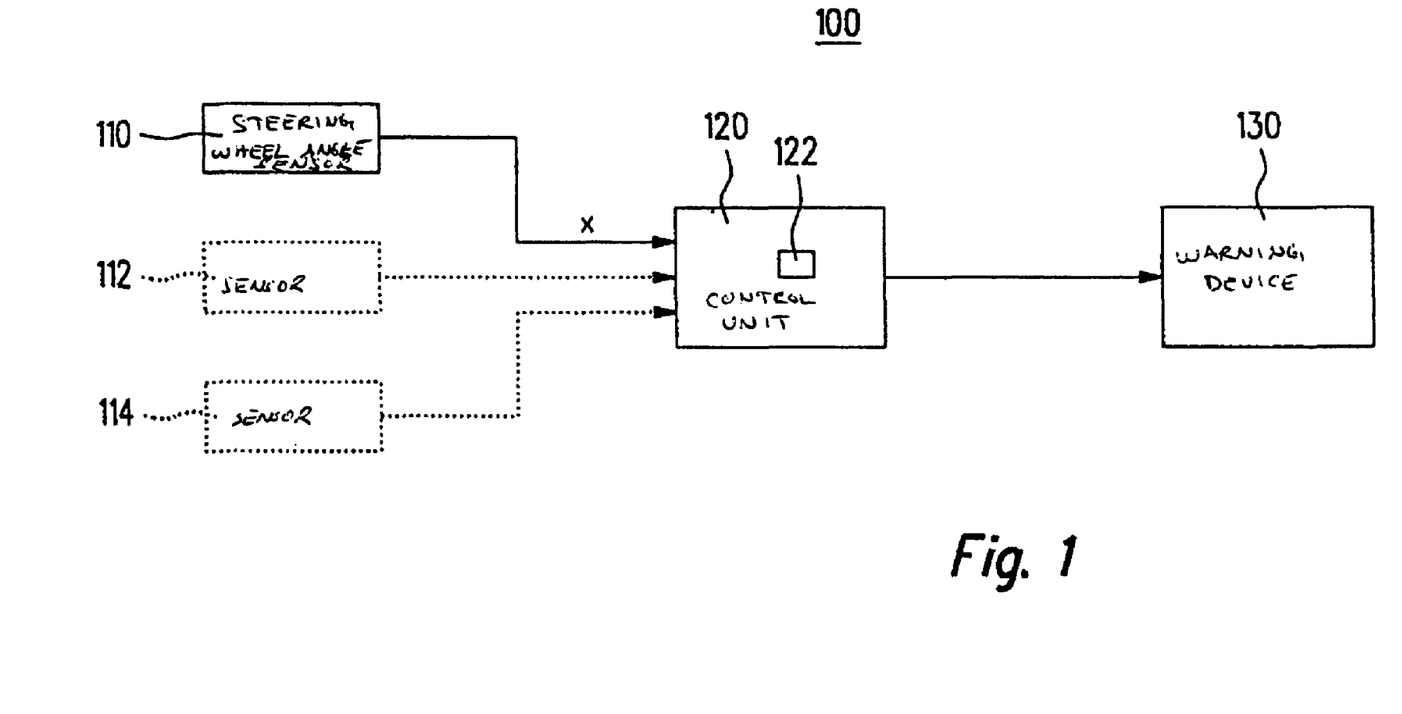
FIG. 1 shows a controller according to the invention.

FIG. 1 shows a controller 100 for carrying out the method according to the invention for identification of inattentiveness by the driver of a vehicle, in particular of a motor vehicle. The controller is preferably mounted in the vehicle (not shown) and includes a steering wheel angle sensor 110 for detecting the current steering wheel angle x, that is to say, the steering movement, caused by the driver. The controller 100 furthermore includes a control unit 120, which is preferably in the form of a microcontroller. The control unit 120 detects a sensor signal, which is produced by the steering wheel angle sensor 110 and represents the steering wheel angle x.

The steering wheel angle x represents a first indicator, which is preferred according to the invention, for inattentiveness by the driver. In addition to the steering wheel angle, the control unit 120 can also, in principle, receive and evaluate further sensor signals from other sensors 112, 114 as further indicators of the inattentiveness by the driver. Such further sensor signals will not be described at this point, but are mentioned further below in the description.

Inattentiveness by the driver is identified by running a computer program 122 in the control unit 120, which program identifies the inattentiveness using a method according to the invention and described in the following that evaluates the steering wheel angle x used as a preferred indicator. If inattentiveness by the driver is found, then it is advantageous for the control unit 120 to drive a warning device 130 in order that it emits audible or visual warning information to the driver. The warning information makes the driver aware of his inattentive behavior in driving of the vehicle, and provides him with the opportunity to re-establish his attention.

Figure 2:
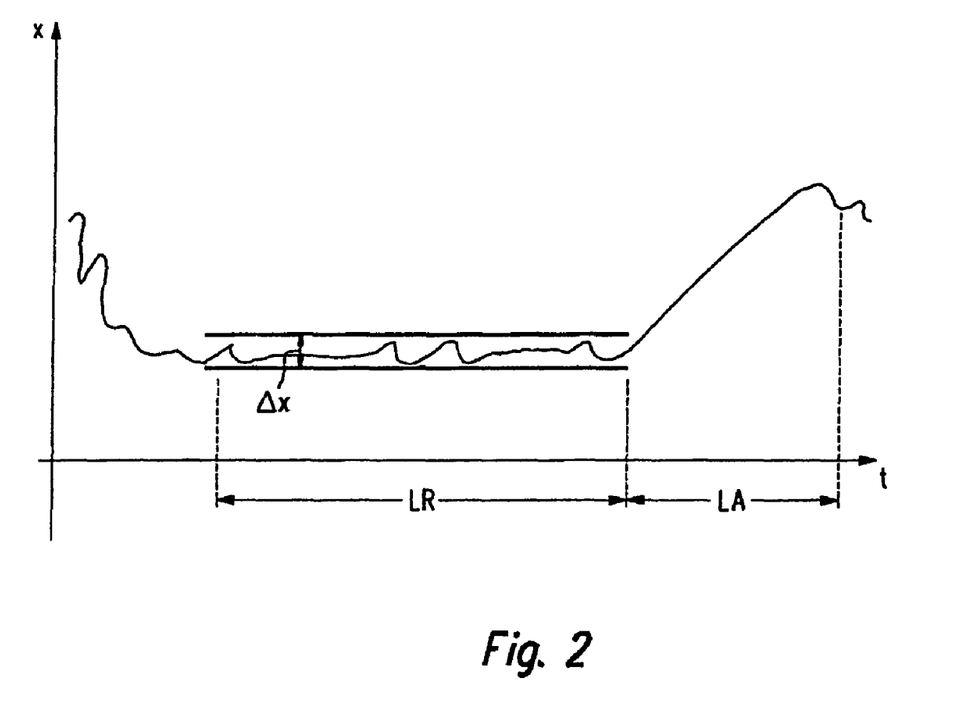
FIG. 2 shows an example of the profile of the steering angle x when driver inattentiveness occurs, according to the invention.

FIG. 2 shows a typical profile of the steering wheel angle, as occurs when inattentiveness by the driver has been identified with the aid of the present invention. To this extent, this profile is typical of the existence of inattentiveness by the driver in which, first of all, he has a steering quiescent phase LR in which he makes no significant changes. In FIG. 2, the steering angle x remains in the deflection range Δx, which is bounded by the two parallel horizontal lines, throughout the steering quiescent phase LR. The presence of inattentiveness in the sense of the invention is then characterized by a very sharp or powerful steering action, which follows this steering quiescent phase. This powerful steering action LA is represented in FIG. 2 by the rapid rise in the steering angle x at the end of the quiescent phase.

Figure 3A:
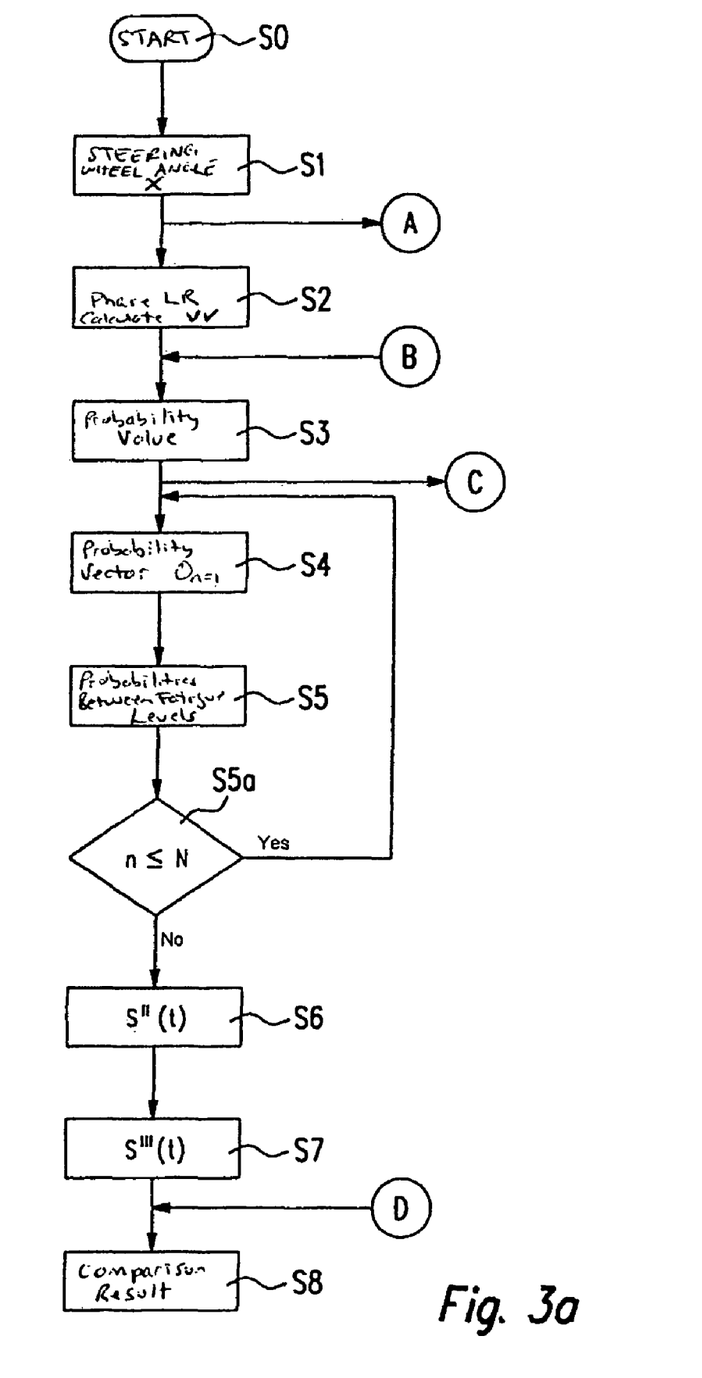
FIG. 3a is a flow chart of the method according to the invention based on a first exemplary embodiment.

FIG. 3 shows the method according to the invention, implemented with the aid of the controller 100 described above. The method steps S0-S8 shown in FIG. 3a first of all represent a first exemplary embodiment of this method. This will be described first of all in the following text in detail and in a related form. The branches A, B, C and D shown in FIG. 3a are irrelevant to this first exemplary embodiment; these will not become relevant until the description of a second exemplary embodiment of the method according to the invention, which follows the description of the first exemplary embodiment.

First Exemplary Embodiment

Following a starting step S0, the first exemplary embodiment as shown in FIG. 3a first of all provides for the detection of a steering movement of the steering wheel of the vehicle, that is to say the detection of the steering behavior of the driver in the form of the steering wheel angle x (method step S1). The steering quiescent phase LR, see FIG. 2, is then identified in a second step S2 on the basis of the detected steering wheel angle x. A variance ratio vv $(x, t_1)$ is then likewise calculated in step 2, as the quotient of a second divided by a first steering wheel angle variance. In this case, the first steering wheel angle variance $v(x, t_1 - \Delta t)$ at an early time $t_1 - \Delta t$ is calculated using the following formula (1):

$$v(x, t_1 - \Delta t) = \mathrm{var}(x(t_1 - \Delta t), \ldots, x(t_1 - \Delta t - T)) = \frac{1}{T} \sum_{t=(t_1 - \Delta t)}^{(t_1 - \Delta t - T)} (x(t) - \bar{x})^2 \quad (1)$$

where:
$x(t_1 - \Delta t)$ represents the steering wheel angle x at the time $t_1 - \Delta t$;

Δt represents a multiple of the sampling interval;
T represents an observation time window;
$t_1 - \Delta t$ represents the observation time;
$\bar{x}$ represents a mean time value of the steering wheel angle x averaged over the observation time window T; and
var represents the mathematical variance function.

The second steering wheel angle variance $v(x, t_1)$ is calculated using the following formula (2):

$$v(x, t_1) = \mathrm{var}(x(t_1), \ldots, x(t_1 - T)) = \frac{1}{T} \sum_{t=(t_1)}^{(t_1 - T)} (x(t) - \bar{x})^2 \quad (2)$$

where the variables have the same meanings as in the formula (1) with the only difference being that they are considered at the observation time $t_1$.

The variance ratio $vv(x, t_1)$ is then calculated from the first and second steering wheel angle variances as follows:

$$vv(x, t_1) = \frac{v(x, t_1)}{v(x, t_1 - \Delta t)} \quad (3)$$

The variance ratio calculated in method step S2 therefore represents a reliable measure of the severity of the inattentiveness of the driver in steering of the vehicle at the time $t_1$, because it effectively records the typical steering behavior of a driver when he is not paying attention. A typical steering behavior when the driver is not paying attention is characterized—as has already been stated above with reference to FIG. 2—by a first steering quiescent phase LR without any steering activity, or with only a minor amount of steering activity, and by a subsequent second steering action phase LA with above-average powerful steering movements. The first phase leads, at the early observation time $t_1 - \Delta t$, to the first variance at a small magnitude. In contrast, the second phase, in particular at the time $t_1$, leads to a considerably greater value for the second variance. Overall, this results in a small value for the denominator and a large value for the numerator, so that, overall, these two effects result in a high value for the variance ratio. As long as the variance ratio is $\leq 1$, this indicates that the driver is not inattentive. Only when the variance ratio assumes a value greater than 1 does this indicate that the driver of the vehicle is not paying sufficient attention to the road traffic.

The value of the variance ratio may, in theory, be indefinitely high. However, indefinitely high values of this type are unsuitable to allow the inattentiveness of the driver to be classified sufficiently accurately.

Figure 4:
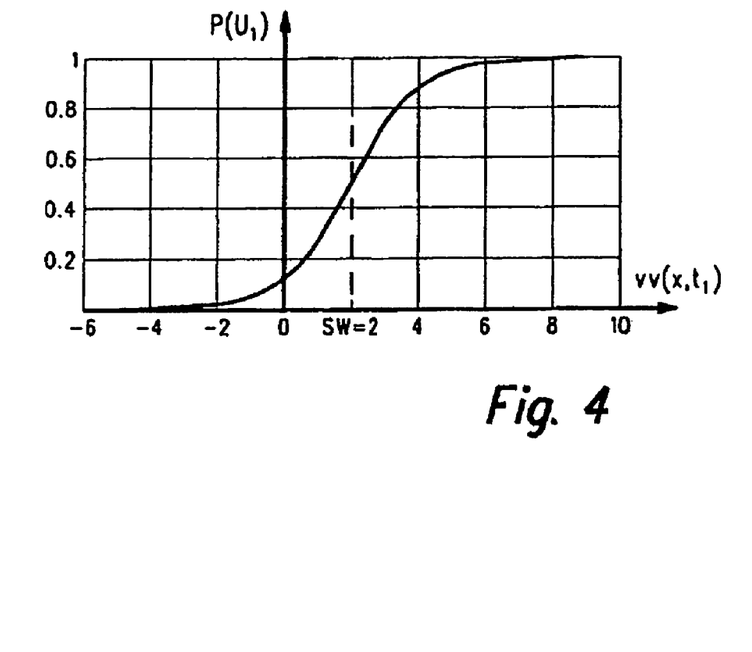
FIG. 4 illustrates a sigmoid function.

In one particular variant of the method according to the invention, the variance ratio is therefore converted to a probability value in a subsequent method step S3. This conversion is preferably carried out with the aid of a sigmoid function, which is illustrated in FIG. 4 and has a suitable predetermined threshold value SW. This threshold value for the sigmoid function illustrated in FIG. 4 is SW=2. This means that a variance ratio $vv(x, t_1)$ (which is plotted on the abscissa in FIG. 4) of 2 indicates a probability $P(U_n)$, where n=1 (first indicator), of 0.5, that is to say of 50%, of the driver of the vehicle having been inattentive at the time $t_1$. As can be seen from the graph of the sigmoid function in FIG. 4, the probability $P(U_1)$ may, in principle, assume a value between 0 and 100%, depending on the magnitude of the variance ratio.

The sigmoid function ensures a "soft" transition from total attention corresponding to a probability value for the instantaneous inattentiveness of 0 to total inattention, corresponding to a value for the inattentiveness of 1=100%. Mathematically, the sigmoid function illustrated in FIG. 4 is calculated using the following formula (4):

$$P(U_1) = \frac{1}{1 + e^{-(vv(x,t_1)-S)}}, \quad (4)$$

where

P(U$_1$) represents the probability of the inattentiveness by the driver in steering the vehicle, with U$_1$ representing an inattentiveness event detected with the aid of the first indicator (steering wheel angle: n=1), and S representing the threshold value.

The evaluations of the steering wheel angle x carried out so far (that is to say up to and including the method step S3) have allowed identification of the presence or absence of inattentiveness by the driver at the time t$_1$. A further evaluation of the knowledge obtained up to this point, preferably with the aid of a dynamic probabilistic model, further allows conclusions to be drawn relating to the possible causes of inattentiveness that have been found. The method steps S4-S6, which will be described in the following text, therefore indicate a method with whose aid, for example, it is possible to determine the probability that fatigue is the cause of the driver inattentiveness that has been detected.

Figure 5:
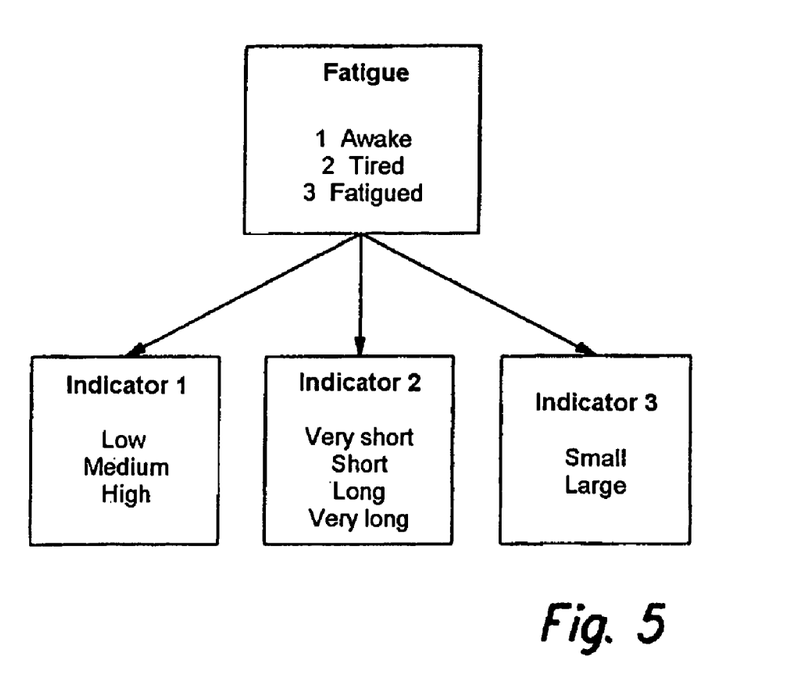
FIG. 5 illustrates a first cause and effect diagram.

This relationship, which has just been described, between fatigue being the cause of inattentiveness in the steering of the vehicle resulting from this is illustrated in FIG. 5. The arrows shown there point from fatigue as the cause to various possible effects, in particular to inattentiveness in the steering of the vehicle (indicator 1). In addition to the effect of inattentiveness, fatigue may, however, also have other observable effects, such as frequent closure of the eyelids (indicator 2) or a delayed reaction capability (indicator 3).

In order to make it possible to deduce driver fatigue from a detected inattentiveness event in the steering of the vehicle, a first probability vector O$_{n=1}$ is, according to the invention, determined in the method step S4, whose elements O$_{n=1, kn=1}$ each represent probability values of the probability value P(U$_1$) occurring in individual, predetermined, and suitably selected extent levels k$_n$, where k$_n \in \{1 \ldots K\}$. The parameter n in this case represents a respectively evaluated indicator, with n=1 representing the steering behavior or the steering wheel angle as an indicator.

Figure 6:
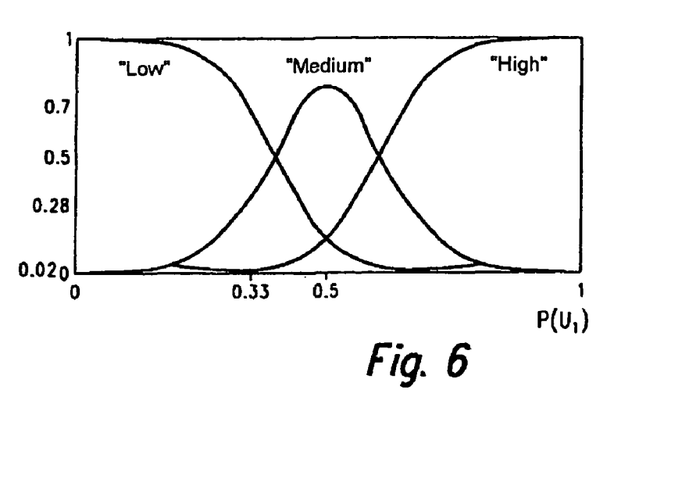
FIG. 6 shows Gaussian distributions for various extent levels in which a probability value, which represents the inattentiveness by the driver, may occur.

FIG. 6 illustrates the process for determination of the first probability vector O$_{n=1}$. In this figure, the probability value P(U$_1$) as determined in the previous method step S3 is plotted between 0 and 100% on the abscissa, representing the probability of inattentiveness by the driver in steering the vehicle at the time t$_1$. The previously determined probability value P(U$_1$) will now be predetermined in the method step S4, and associated with suitable defined extent levels k$_n \in \{1 \ldots K_1\}$. In the exemplary embodiment shown in FIG. 6, three extent levels were predetermined, "low" (k$_1$=1), "medium" (k$_1$=2) and "high" (k$_1$=3) (see FIG. 5) for the indicator 1, and each is represented by their own Gaussian function in FIG. 6. The number of extent levels for the indicator 1 in this example is thus k$_1$=3.

The number and parameters of these Gaussian functions for the respective extent levels, such as their center points or their variances, can be configured appropriately depending on the application. As can be seen from FIG. 6, a probability of 70% of this probability value occurring with only a small extent would be associated, after carrying out the method step S4, with a probability value P(U$_1$) (assumed by way of example) of 0.33 for the inattentiveness by the driver. There is a 28% probability of the calculated probability value occurring with a medium extent, while there is a probability of only 2% of the calculated probability value occurring with a high extent.

In other words, in the case of the example illustrated in FIG. 6 for the assumed probability value of 0.33 for the inattentiveness by the driver at the time t$_1$, results in the statement that the probability of inattentiveness by the driver having only a low extent occurred with a probability of 70%, that is to say there was a 70% probability that the driver was paying attention. This also results in the statement that there was a probability of 28% that the driver was paying medium attention, and that there was a probability of only 2% of him being highly inattentive.

An indefinite number of fatigue levels can now be defined in the next method step S5, and conditional probabilities between these levels as well as the observed steering inattentiveness event can now be allocated. In the example shown in FIG. 5, a total of three fatigue levels "awake", "tired" and "fatigued" are provided. Conditional probabilities can then likewise be allocated, also in the method step S5, in the form of a matrix B between each of these fatigue levels and one of the extent levels described above. This matrix B covers a total number of matrix elements, which is calculated from the product of the number of extent levels multiplied by the number of predetermined fatigue levels. If there are three extent levels "low", "medium" and "high" for the steering inattentiveness event, the three fatigue levels mentioned above result in a total number of 3*3=9 conditional probabilities for the matrix B. By way of example, one of these probabilities indicates how high the probability is of a steering inattentiveness event in the "high" extent level occurring, given that the probabilistic model in the first fatigue level is "awake". These conditional probabilities can be configured appropriately.

With the probability vector O$_{n=1}$ as determined in step S4, and the calculated matrix B, it is now possible to determine, in a method step S6, a fatigue probability vector S' associated with individual, predetermined and suitably selected fatigue levels, whose elements each represent probabilities P (fatigue level) of the detected inattentiveness by the driver in steering the vehicle. The fatigue probability vector S' is calculated using the following formula (5):

$$S'(t) = O_1^T \cdot B_1 \quad (5)$$

where

O$_{n=1}^T$ represents the transpose of the first probability vector; and

B$_1$ represents the matrix B for the detected indicator for steering inattentiveness, represented by the index 1.

The calculation rule (5) just described for calculation of the fatigue probability vector S' has the disadvantage that it is based only on an evaluation of the steering wheel angle x as an indicator (n=1). Other possible observable effects of fatigue, such as those indicated in FIG. 5 by the indicators 2 (for example eyelid closure frequency) or the indicator 3 (for example reaction time) are not included in the formula 5 for calculation of the fatigue probability vector.

However, it is also possible to use these indicators 2 and 3, as well as further suitable indicators n, for example the yaw angle of the vehicle, the distance from the vehicle in front or the leaving of a lane, to the extent that these can be measured, for calculation of a more precise fatigue probability vector S". The method steps S4 and S5 which have just been described must then be carried out in each case not only for the observed steering angle as the indicator n=1, but also for further desired indicators such as the eyelid closure behavior (n=2) and/or reaction time (n=3), etc., separately (method step S5a). In the course of method step S4, an individual number of extent levels $k_n$ (where $k_n=1 \ldots K$) must then be defined individually for each indicator n. This number of extent levels $k_n$ then, in each case, corresponds to the number of elements in a probability vector $O_n$ associated with the respective indicator. These elements $O_{n,kn}$, in each case, represent probabilities $P(O_{n,kn})$ of probability values $P(U_n)$ for the other inattentiveness indicators $n=2 \ldots N$ occurring in addition to the steering inattentiveness $n=1$ in the individual extent levels $k_n$ which are predetermined and suitably selected individually for the indicators.

A corresponding matrix $B_n$ can then also be predetermined individually for these further indicators n, corresponding to the method step S5, once again. The more precise fatigue probability vector S" is then calculated on the basis of the data that is then available in step S6, using the following formula (6):

$$S''(t) = \prod_{n=1}^{N} O_n^T \cdot B_n, \qquad (6)$$

where:
n represents the n-th indicator for the inattentiveness by the driver,
$k_n$ represents the k-th element of the vector $O_n$ or the k-th extent level for the indicator n;
$O_n^T$ represents the transpose of a probability vector;
$B_n$ represents the matrix of conditional probabilities between individual predetermined fatigue levels and an inattentiveness event which is indicated by the indicator n; and
N represents the number of indicators used.

In the two variants which have been described so far for calculation of the fatigue probability vector S, only the severity of a detected inattentiveness event has been traced back to the most probable actual fatigue level, be this on the basis of a detected steering inattentiveness event or else on the basis of additionally detected events, such as increased eyelid closure behavior or shortened reaction time. Further details of this process of tracing back from the observed inattentiveness to an existing fatigue level as the cause of this inattentiveness can be achieved by taking account not only the severity of the inattentiveness event, but also the most probable fatigue level determined in a previous time interval. This ensures that once an inattentiveness event has been detected, or has been detected for the first time, this does not in itself lead immediately to the conclusion that the fatigue level is high. This would not be consistent with the actual characteristic of fatigue since, in principle, fatigue is a phenomenon which does not occur suddenly, but builds up slowly only over the course of a certain period of time.

In the case of the three fatigue levels mentioned above and described in FIG. 5, the change from one fatigue level to another is therefore provided with different conditional probabilities. These conditional probabilities are preferably predetermined in a suitable manner in the form of a matrix A in the course of the probabilistic model. The conditional probabilities in the matrix A are intended, in particular, to express the fact that, for example, a direct transition from fatigue level 1 "awake" to fatigue level 3, "fatigued" is considerably less probable than a direct transition from level 1 to level 2, "tired", in which, in comparison to level 1, initial adverse effects in terms of the attention of the driver can now be identified. The configuration of the matrix A should also take account of the fact that the transitions from being awake to a state of greater fatigue take place with different conditional probabilities, in the same way as the transitions from a fatigued state to being awake.

With the most probable fatigue level determined in a previous time period also being taken into account, the fatigue probability vector S''', which has once again been made more precise in this way, is then calculated in step S7 using the following recursive formula (7):

$$S'''(t_1) = S''(t_1) \cdot A \cdot S'''(t_1-1) \qquad (7),$$

where
$S''(t_1)$ represents the more precise fatigue vector S" without consideration of the most probable fatigue level determined in the previous time interval;
A represents the matrix of conditional probabilities between a fatigue level in the most recent time interval and a current fatigue level; and
$S'''(t_1-1)$ represents the more precise fatigue vector S''' in the time period $t_1-1$.

It is recommended that an initial value of $S'''(0)=(1, 0, 0)^T$ be used as the third variant in order to start the recursive calculation of the more precise fatigue probability vector S''' using the formula (7).

In other words, the more precise calculation of the fatigue probability vector S''' using the formula (7) results in the fatigue vector being smoothed over time, and/or prevents an inattentiveness event which has been identified for the first time immediately leading to a sudden change in the fatigue level which is assumed to be the most probable cause of the detected inattentiveness event. Suitable configuration of, in particular, the matrix A also ensures that, conversely, a high degree of attention by the driver, which is detected suddenly, does not immediately lead to a low fatigue level if a very high fatigue level has been determined to be the probable cause of detected inattentiveness immediately before this.

Figure 7:
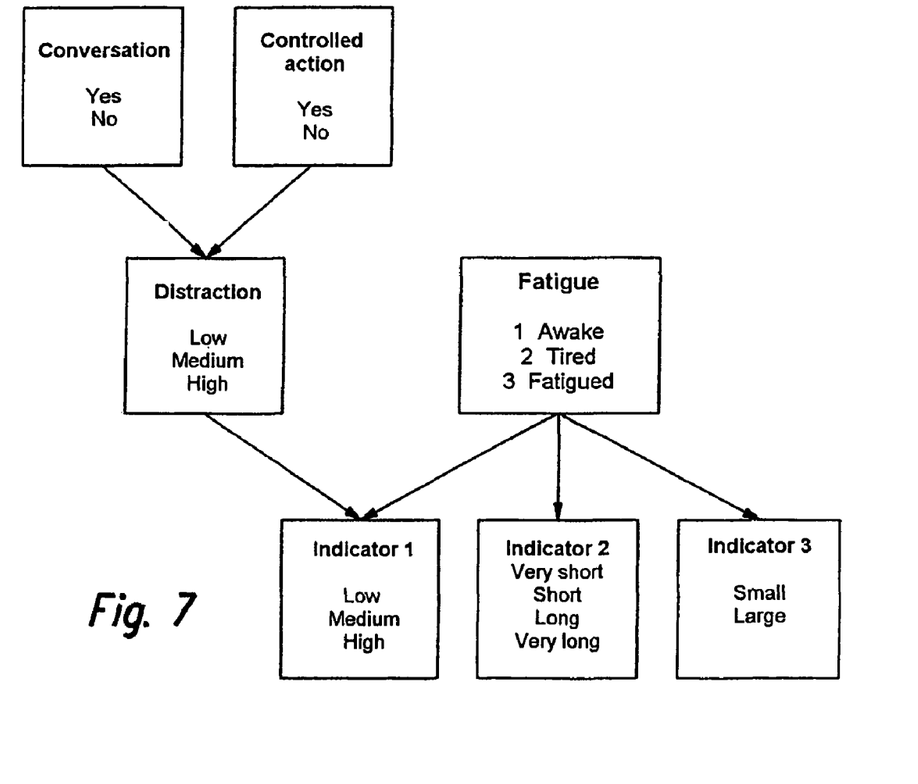
FIG. 7 illustrates a second cause and effect diagram.

The method described so far has always had the aim of deducing a certain fatigue level as the cause of the detected inattentiveness on the basis of detected steering inattentiveness and, optionally, also on the basis of further indicators for inattentiveness by the driver. This is illustrated once again in graphical form in FIG. 7, where the arrows point from a cause to an effect. However, the directions of the arrows in FIG. 7 also show that, according to the model on which this is based, that fatigue is immediately the sole cause for the indicators 2, that is to say the eyelid closing behavior, and 3, that is to say shortened reaction time, but that this need not be the only cause of detected steering inattentiveness. In fact, in addition to or as an alternative to fatigue, a given temporary distraction of the driver may also be the cause of detected driver steering inattentiveness. The reason for distraction may in turn be, for example, a conversation being held with the front seat passenger or an action carried out on a control element, for example the radio or the glove compartment in the vehicle. If, in addition to the previously mentioned inattentiveness events or indicators, possible causes for distraction are also additionally detected with the aid of suitable sensors, such as a microphone 112 or a camera 114 (see FIG. 1), then these detected events can be evaluated with the aid of the probabilistic model in order to make a statement about the probability with which it can be assumed that the driver has been distracted, for example owing to a conversation being held or a control action being carried out, and the probability of fatigue being the cause of the observed inattentiveness.

The driver inattentiveness, which is detected by one of the variants of the first exemplary embodiment, is finally compared with an error criterion, in particular with a respectively suitably predetermined threshold value, in order to then output a warning signal to the driver on the basis of the result of this comparison (method step S8 as shown in FIG. 3a).

Second Exemplary Embodiment

Figure 3B:
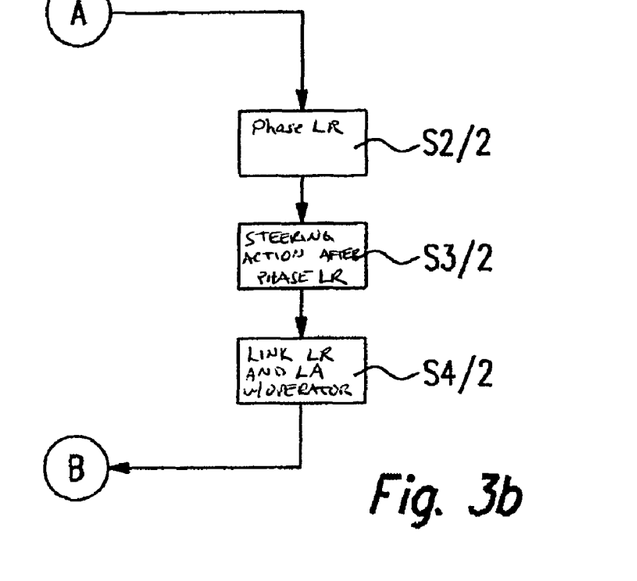
FIGS. 3b and 3c, in conjunction with FIG. 3a, are flow charts of the method according to the invention based on a second exemplary embodiment.

The second exemplary embodiment of the method according to the invention is admittedly, in principle, independent of the first exemplary embodiment, but has individual method steps which are identical to the individual method steps from the first exemplary embodiment. One fundamental difference between the first and the second exemplary embodiments is that, in the first exemplary embodiment, the identification of a steering action LA and the calculation of a logical operation result between the extent of the steering quiescent phase and the extent of the steering action coincide in the form of the calculation of the variance ratio. In contrast, the second exemplary embodiment offers the advantage that not only the steering quiescent phase LR but also the subsequent steering action LA and the logical linking according to the invention of the extents of these two phases can, in each case, be carried out separately as separate method steps, as will be described in more detail in the following text with reference to FIGS. 3a, 3b and 3c.

After a starting step S0, the second exemplary embodiment as shown in FIG. 3a first of all provides for the detection of the steering movement of the steering wheel of the vehicle, that is to say the detection of the steering behavior of the driver in the form of the steering wheel angle x (method step S1). To this extent, the first and the second exemplary embodiments still coincide. For the second exemplary embodiment, this is now not followed by the method step S2 as shown in FIG. 3a, but rather the method branches via the mark A to FIG. 3b, while the extent of the steering quiescent phase is first of all determined in the method step S2/2. The extent of the steering quiescent phase means, in particular, its time duration. A steering quiescent phase exists for as long as the steering angle of the vehicle is within a predetermined steering wheel angle interval $\Delta x$ as shown in FIG. 2. The time period for which this situation lasts then represents the extent of the steering quiescent phase LR.

The extent of a steering action following the detected steering quiescent phase is then detected in a method step S3/2. The maximum gradient of the steering angle, which then occurs is determined for this purpose. In FIG. 2, this gradient is illustrated in the form of the gradient of the steering angle, how it occurs, once the steering wheel angle has left the steering wheel angle interval $\Delta x$.

The extent of the steering quiescent phase and of the steering action are then linked to one another in the method step S4/2 by means of a multidimensional operator. The multidimensional operator may be a family of characteristics, a weighting function or a logical decision function. The result of this use of the multidimensional operator then represents a suitable measure for the severity of the inattentiveness of the driver in steering the vehicle. The logical linking of the two extents which have been mentioned is, however, preferably carried out only when it has been found in the steps S2/2 or S3/2 (which were carried out prior to this) that the extent of the steering quiescent phase in the form of its time period is greater than a predetermined minimum time period, and the maximum gradient of the steering wheel angle is greater than a predetermined gradient threshold value. Otherwise, the extents of the steering quiescent phase and of the steering action are not regarded by the method according to the invention as being sufficiently strongly pronounced in order to allow the deduction of driver inattentiveness as a result of their combined presence.

The multidimensional operator is preferably dimensioned on the basis of the current speed of the vehicle and/or on the basis of the dynamics of the driving style of the vehicle driver. Specifically, this means that the evaluation of the detected extents of the steering quiescent phase and of the steering action take account of the fact that steering movements are typically less at high vehicle speeds than at low speeds. Matching to the driving style of the driver prevents a hectic steering movement which is carried out deliberately, for example by a rally driver, in conjunction with a previously detected supposed steering quiescent phase, incorrectly being interpreted as driver inattentiveness.

The logical operation result determined in method step S4/2 according to the second exemplary embodiment can now be evaluated and processed further in various ways.

A first option is to normalize this with the aid, for example, of the sigmoid function. This option is shown by the mark B in FIG. 3b, which branches to the input of the method step S3 in FIG. 3a. It is then possible to carry out not only the method step S3, but then also all the further method steps S4 to S8, as described above with reference to FIG. 3a.

Figure 3C:
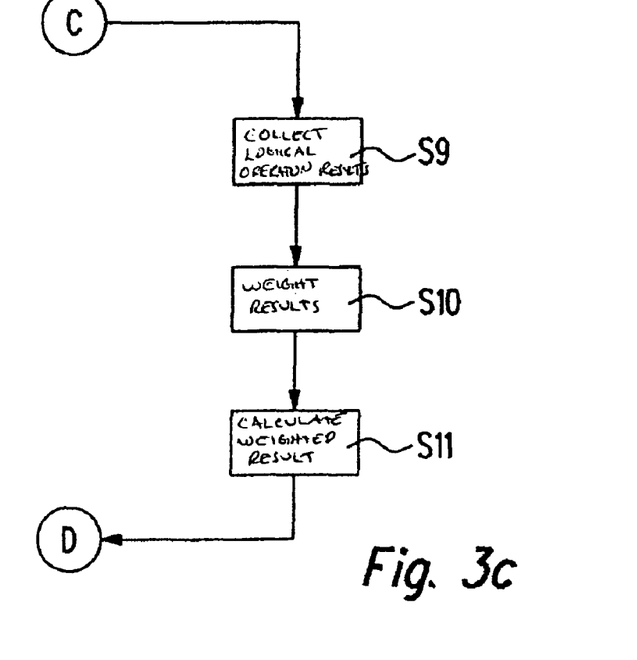

A second option for further processing of the logical operation result obtained in the method step S4/2 admittedly once again includes the normalization process with the aid of the sigmoid function in method step S3, but the evaluation process does not then continue further in accordance with method step S4 and so on. Rather, as is indicated by the mark C in FIG. 3a, the further processing continues in method step S9, as shown in FIG. 3c. This step indicates that the calculation of the logical operation result which has already been carried out, irrespective of whether this was in accordance with the first exemplary embodiment in step 2 or in accordance with the second exemplary embodiment in step S4/2, should be carried out more than once during a predetermined measurement time interval. The repeated calculating of the logical operation results at different times ti where i=1–I throughout the measurement time interval leads to a large number of logical operation results, preferably being available at the end of the measurement time interval. These logical operation results are preferably (as already described) tapped off at the output of the method step S3, because they are then in a normalized form. However, alternatively, the logical operation results which have been obtained directly in the method steps S2 and S4/2 can also be collected and stored directly in method step S9. These logical operation results are then individually weighted in the method step S10, by allocating a weighting factor to each of these results. These weighting factors represent the respective driving situation of the vehicle or the current distraction of the driver, in each case at a time to which the logical operation result relates.

Then, finally, a weighted logical operation result is calculated in the method step S11 by mathematical, preferably arithmetic, weighted averaging of the logical operation results obtained during the measurement time interval, taking into account the weighting factors associated with them.

The weighting factors are defined taking into account the time of day, that is to say circadian influencing factors and/or the time since the start of the journey. The weighted result of the logical operation provides a very reliable measure which, in particular, is relatively simple and fast, for the severity of the inattentiveness of the driver while driving the vehicle. This averaged result of the logical operation is then preferably subjected to an error criterion, as in FIG. 3c in conjunction with FIG. 3a via the mark D in the method step S8, and is evaluated in order to generate a warning signal for the driver. The error criterion is satisfied when the sum of all of the logical operation results calculated in the most recent x minutes, in each case weighted with their individual weighting factors, exceeds a predetermined threshold value.

The second option, as described above, for further processing of the logical operation result obtained in the method step S4/2 according to the second exemplary embodiment, by means of the steps S9 to S11, is also appropriate, in the same way, for the logical operation result obtained in the method step S2 according to the first exemplary embodiment.

A third option for further processing of the logical operation result from step S2 or from step S4/2 is to preferably carry out the steps S4 to S7 and S9 to S11 in parallel, in time.

The two exemplary embodiments of the method according to the invention, in all of their variants, are preferably implemented in the form of at least one computer program. If required, the computer program may be stored together with further computer programs in a data storage medium. The data storage medium may be a floppy disk, a compact disk, a so-called flash memory or the like. The computer program which is stored in the data storage medium can then be sold as a product to a customer. As an alternative to transferring it in the form of a data storage medium, it is also possible to transmit it via a communications network, in particular the Internet.

The invention claimed is:

1. A method for identifying when a driver of a vehicle is not paying attention, the method comprising the acts of:
   detecting movement of a steering wheel of the vehicle as a steering wheel angle x;
   identifying a steering quiescent phase;
   determining an extent of the steering quiescent phase by evaluating at least one of the steering wheel angle x and a time variation of the steering wheel angle x, said extent of the steering quiescent phase being a time duration in which the steering wheel angle x remains within a predetermined steering wheel angle interval;
   identifying a steering action following the steering quiescent phase and determining an extent of the steering action by evaluating the rate of change of the steering wheel angle x;
   logically linking the extent of the steering quiescent phase and the extent of the steering action using a multidimensional operator that comprises one of i) a family of characteristics, ii) a weighting function and iii) a logical decision function; and
   assessing a result of said logical linking as a measure of a severity of inattentiveness by the driver while steering the vehicle only when the extent of the steering quiescent phase is greater than a predetermined minimum time period and a maximum gradient of the steering wheel angle exceeds a predetermined gradient threshold value.

2. A computer product, comprising a computer readable medium having program code for a controller for identifying inattentiveness by a driver of a vehicle, wherein the program code performs the method of claim 1.

3. A data storage medium, comprising the computer product as claimed in claim 2.

4. A controller for identifying inattentiveness by a driver of a vehicle, comprising:
   a steering wheel angle sensor for detecting a current steering wheel angle of the vehicle;
   a microcontroller control unit for carrying out the method as claimed in claim 1 in response to the detected steering wheel angle; and
   a warning device for outputting audible and/or visual warning information to the driver when inattentiveness has been found when carrying out the method by the microcontroller control unit.

5. The method as claimed in claim 1, wherein the extent of the steering action following a previous steering quiescent phase is determined in the form of a maximum gradient of the steering wheel angle which then occurs.

6. The method as claimed in claim 1, wherein the multidimensional operator is dimensioned on the basis of at least one of a vehicle speed and a driver's driving style dynamics.

7. The method as claimed in claim 1, wherein in a subsequent act, a result of said logical linking is mapped in the form of the variance ratio $vv(x, t)$ or of a multidimensional operator, with the aid of a sigmoid function, onto a probability value $P(U_1)$ between 0 and 100%, which represents the inattentiveness by the driver in steering the vehicle at the time $t_1$.

8. The method as claimed in claim 1, wherein for further assessing driver fatigue, the method further comprising the acts of:
   determining a first probability vector $O_{n=1}$, whose elements $O_{n=1,k1}$ each represent probability values $P(O_{1,k1})$, of the probability value $P(U_1)$ occurring in individual, predetermined and selected extent levels $k_1$, where $k_1 \in \{1 \ldots K_1\}$; and
   determining a fatigue probability vector $S'$, whose elements each represent fatigue level probabilities P, of the detected inattentiveness by the driver in steering the vehicle being associated with individual, predetermined and suitably selected fatigue levels, using the following formula:

$$S'(t) = O_1^T \cdot B_1;$$

with $O^T_1$ representing a transpose of the first probability vector;
$B_1$ a matrix B representing predetermined conditional probabilities with respect to the inattentiveness, represented by the indicator n=1; and
$K_1$ representing the number of extent levels for the indicator n=1.

9. A method for identifying when a driver of a vehicle is not paying attention, the method comprising the acts of:
   detecting movement of a steering wheel of the vehicle as a steering wheel angle x;
   identifying steering quiescent phase;
   determining a magnitude of an extent of the steering quiescent phase by evaluating at least one of the steering wheel angle x and a rate of change of the steering wheel angle x;
   identifying a steering action following the steering quiescent phase and determining a magnitude of an extent of the steering action by evaluating the rate of change of the steering wheel angle x; and
   assessing a result of a logical link between the extent of the steering quiescent phase and the extent of the steering action to determine a measure of a severity of inattentiveness by the driver while steering the vehicle; wherein,
   the extent of the steering quiescent phase is determined for at least one of a time $t_1 - \Delta t$ in a form of a first steering wheel angle fluctuation and for a time $t_1$ in a form of a second steering wheel fluctuation, in each case based on the detected steering wheel angle x;
   the first steering wheel angle fluctuation is calculated in the form of a steering wheel angle variance $v(x, t_1 - \Delta t)$ using the following formula:

$$v(x, t_1 - \Delta t) = \text{var}(x(t_1 - \Delta t), \ldots, x(t_1 - \Delta t - T)) = \frac{1}{T} \sum_{t=(t_1-\Delta t)}^{((t_1-\Delta t)-T)} (x(t) - \bar{x})^2$$

where:

represents the steering wheel angle x at the time $t_1 - \Delta t$;
$\Delta t$ represents a multiple of the sampling interval;
represents an observation time window;
$t_1 - \Delta t$ represents an observation time;
$\bar{x}$ represents a mean time value of the steering wheel angle x averaged over the observation time window T; and
var represents a mathematical variance function; and
    the second steering wheel angle fluctuation in the form of a steering wheel angle variance $v(x, t_1)$ is calculated using the following formula:

$$v(x, t_1) = \text{var}(x(t_1), \ldots, x(t_1 - T)) = \frac{1}{T} \sum_{t=(t_1)}^{(t_1-T)} (x(t) - \bar{x})^2$$

where the variables have the same meanings; and
    the extent of the steering action, and the logical linking of the steering quiescent phase and the steering action, are determined by formation of a variance ratio $vv(x, t_1)$ as a quotient of the second steering wheel angle variance divided by the first.

10. The method as claimed in claim 9, wherein the variance ratio $vv(x, t_1)$ is calculated in accordance with the following formula:

$$vv(x, t_1) = \frac{v(x, t_1)}{v(x, t_1 - \Delta t)}.$$

11. The method as claimed in claim 9, wherein in a subsequent act, a result of the logical link operation is mapped in the form of the variance ratio $vv(x, t)$ or of a multidimensional operator, with the aid of a sigmoid function, onto a probability value $P(U_1)$ between 0 and 100%, which represents the inattentiveness by the driver in steering the vehicle at the time $t_1$.

12. The method as claimed in claim 11, wherein for further assessing driver fatigue, the method further comprising the acts of:
    determining a first probability vector $O_{n=1}$, whose elements $O_{n=1,k1}$ each represent probability values $P(O_1, k1)$, of the probability value $P(U_1)$ occurring in individual, predetermined and selected extent levels $k_1$, where $k_1 \in \{1 \ldots K_1\}$; and
    determining a fatigue probability vector S', whose elements each represent fatigue level probabilities P, of the detected inattentiveness by the driver in steering the vehicle being associated with individual, predetermined and suitably selected fatigue levels, using the following formula:

$$S'(t) = O_1^T \cdot B_1;$$

with
$O_1^T$ representing a transpose of the first probability vector;
$B_1$ a matrix B representing predetermined conditional probabilities with respect to the inattentiveness, represented by the indicator n=1; and
$K_1$ representing the number of extent levels for the indicator n=1.

13. The method as claimed in claim 12, further comprising the acts of:
    determining further probability vectors $O_{n=2} \ldots O_{n=N}$, whose elements $O_{n,kn}$ were $k_n = 1 \ldots K_n$, each representing probabilities $P(O_{n,kn})$ of the probability values $P(U_n)$ occurring for other inattentiveness indicators n=2 . . . N for the driver, in addition to the steering inattentiveness n=1 and an eyelid closure behavior n=2 or a reaction time n=3, in individual extent levels $k_n$, which are predetermined individually for the inattentiveness indicators, and
    calculating the fatigue probability vector S" using the following formula:

$$S''(t) = \prod_{n=1}^{N} O_n^T \cdot B_n$$

where
N represents the n-th indicator for the inattentiveness by the driver;
$O_n^T$ represents the transpose of the further probability vectors;
$B_n$ represents the matrix B for the indicator n; and
N represents the number of indicators.

14. The method as claimed in claim 12, further comprising:
storing the fatigue probability vector S'''(t−1); and
calculating a more precise fatigue probability vector S'''(t) using the following formula:

$$S'''(t) = S''(t) \cdot A \cdot S'''(t-1),$$

where
A represents a matrix of conditional probabilities between a fatigue level from a previous time step and a current fatigue level.

15. The method as claimed in claim 13, further comprising:
storing the fatigue probability vector S'''(t−1); and
calculating a more precise fatigue probability vector S'''(t) using the following formula:

$$S'''(t) = S''(t) \cdot A \cdot S'''(t-1),$$

where
A represents a matrix of conditional probabilities between a fatigue level from a previous time step and a current fatigue level.

16. The method as claimed in claim 13, wherein, in addition to the steering inattentiveness and optional further indicators for the inattentiveness by the driver, the method determines whether the driver is holding a conversation or is using a control element; and
    further wherein said events are evaluated using a probabilistic model in order to make a statement about the probability with which it is assumable that the driver has been distracted, on the basis of the conversation or the control action, and the probability of driver fatigue being the cause of such observed inattentiveness.

17. The method as claimed in claim 14, wherein, in addition to the steering inattentiveness and optional further indicators for the inattentiveness by the driver, the method determines whether the driver is holding a conversation or is using a control element; and
    further wherein said events are evaluated using a probabilistic model in order to make a statement about the probability with which it is assumable that the driver has been distracted, on the basis of the conversation or the control action, and the probability of driver fatigue being the cause of such observed inattentiveness.

18. The method as claimed in claim 9, wherein:
the logical link operation is carried out at different times ti, where i=1–I during a predetermined measurement time interval;
results of the logical operations relating to the times ti are, in each case, stored together with associated weighting factors which represent the driving situation of the vehicle or the current distraction of the driver, in each case relating to the time ti; and
a weighted result of the logical operation is calculated by arithmetic averaging of the results stored during the measurement time interval, taking into account the associated weighting factors.

19. The method as claimed in claim 18, wherein the weighting factors are calculated taking into account at least one of circadian influencing factors and the time since a journey started.

20. The method as claimed in claim 18, further comprising:
outputting information, in a form of an audible or visual warning message to the driver of the vehicle, when the preferably weighted result exceeds a predetermined threshold value.

21. A method for identifying when a driver of a vehicle is not paying attention, the method comprising the acts of:
detecting movement of a steering wheel of the vehicle as a steering wheel angle x;
identifying a steering quiescent phase;
determining a magnitude of an extent of the steering quiescent phase by evaluating at least one of the steering wheel angle x and a rate of change of the steering wheel angle x;
identifying a steering action following the steering quiescent phase and determining a magnitude of an extent of the steering action by evaluating the rate of change of the steering wheel angle x; and
assessing a result of a logical link between the extent of the steering quiescent phase and the extent of the steering action to determine a measure of a severity of inattentiveness by the driver while steering the vehicle;
wherein, the extent of the steering quiescent phase is determined as that time period during which the steering wheel angle remains within a predetermined steering wheel angle interval ($\Delta x$).

22. The method as claimed in claim 21, wherein the steering wheel angle interval is predetermined on a basis of a current speed of the vehicle.

23. The method as claimed in claim 21, wherein the extent of the steering action following a previous steering quiescent phase is determined in the form of a maximum gradient of the steering wheel angle which then occurs.

24. The method as claimed in claim 23, wherein the logical linking between the extent of the steering quiescent phase and the extent of the steering action at a time t1 is produced by using a multidimensional operator only when the extent of the steering quiescent phase in the form of its time period is greater than a predetermined minimum time period and the maximum gradient of the steering wheel angle exceeds a predetermined gradient threshold value.

25. The method as claimed in claim 24, wherein the multidimensional operator represents a family of characteristics, a weighting function or a logical decision function.

26. The method as claimed in claim 24, wherein the multidimensional operator is dimensioned on the basis of at least one of a vehicle speed and a driver's driving style dynamics.

27. The method as claimed in claim 25, wherein the multidimensional operator is dimensioned on the basis of at least one of a vehicle speed and a driver's driving style dynamics.

28. The method as claimed in claim 24, wherein in a subsequent act, a result of the logical link operation is mapped in the form of the variance ratio vv(x, t) or of a multidimensional operator, with the aid of a sigmoid function, onto a probability value $P(U_1)$ between 0 and 100%, which represents the inattentiveness by the driver in steering the vehicle at the time $t_1$.

29. The method as claimed in claim 28, wherein for further assessing driver fatigue, the method further comprising the acts of:
determining a first probability vector $O_{n=1}$, whose elements $O_{n=1,k1}$ each represent probability values $P(O_{1,k1})$, of the probability value $P(U_1)$ occurring in individual, predetermined and selected extent levels $k_1$, where $k_1 \in \{1 \ldots K_1\}$; and
determining a fatigue probability vector S', whose elements each represent fatigue level probabilities P, of the detected inattentiveness by the driver in steering the vehicle being associated with individual, predetermined and suitably selected fatigue levels, using the following formula:

$$S'(t) = O_1^t \cdot B_1;$$

with
$O^T_1$ representing a transpose of the first probability vector;
$B_1$ a matrix B representing predetermined conditional probabilities with respect to the inattentiveness, represented by the indicator n=1; and
$K_1$ representing the number of extent levels for the indicator n=1.

30. The method as claimed in claim 29, further comprising the acts of:
determining further probability vectors $O_{n=2} \ldots O_{n=N}$, whose elements $O_{n,kn}$ were $k_n=1 \ldots K_n$, each representing probabilities $P(O_{n,kn})$ of the probability values $P(U_n)$ occurring for other inattentiveness indicators n=2 \ldots N for the driver, in addition to the steering inattentiveness n=1 and an eyelid closure behavior n=2 or a reaction time n=3, in individual extent levels $k_n$, which are predetermined individually for the inattentiveness indicators, and
calculating the fatigue probability vector S" using the following formula:

$$S''(t) = \prod_{n=1}^{N} O_n^T \cdot B_n$$

where
N represents the n-th indicator for the inattentiveness by the driver;
$O_n^T$ represents the transpose of the further probability vectors;
$B_n$ represents the matrix B for the indicator n; and
N represents the number of indicators.

* * * * *